(12) United States Patent
Fridman et al.

(10) Patent No.: US 7,622,623 B2
(45) Date of Patent: Nov. 24, 2009

(54) CATALYTICALLY INACTIVE HEAT GENERATOR AND IMPROVED DEHYDROGENATION PROCESS

(75) Inventors: Vladimir Fridman, Louisville, KY (US); Jay S. Merriam, Louisville, KY (US); Michael A. Urbancic, Louisville, KY (US)

(73) Assignee: Sud-Chemie Inc., Louisville, KY (US)

( * ) Notice: Subject to any disclaimer, the term of this patent is extended or adjusted under 35 U.S.C. 154(b) by 552 days.

(21) Appl. No.: 11/218,949

(22) Filed: Sep. 2, 2005

(65) Prior Publication Data

US 2007/0054801 A1   Mar. 8, 2007

(51) Int. Cl.
| | |
|---|---|
| C07C 2/76 | (2006.01) |
| C07C 2/78 | (2006.01) |
| C07C 5/08 | (2006.01) |
| C07C 11/00 | (2006.01) |
| C07C 5/09 | (2006.01) |
| C07C 5/327 | (2006.01) |
| B01J 23/00 | (2006.01) |
| B01J 20/00 | (2006.01) |

(52) U.S. Cl. ............... 585/630; 585/602; 585/616; 585/627; 585/629; 502/305; 502/318; 502/415

(58) Field of Classification Search ......... 502/102–106, 502/300, 305–307, 318, 320, 329, 353, 415; 585/602, 616, 617, 629

See application file for complete search history.

(56) References Cited

U.S. PATENT DOCUMENTS

| | | | |
|---|---|---|---|
| 2,399,678 A | 5/1946 | Houdry | |
| 2,419,997 A | 5/1947 | Houdry | |
| 2,423,029 A | 6/1947 | Houdry | |
| 2,423,835 A | 7/1947 | Houdry | |
| 3,488,402 A | 1/1970 | Michaels et al. | |
| 3,665,049 A * | 5/1972 | Cornelius et al. | 585/662 |
| 3,754,051 A | 8/1973 | Suzukawa | |
| 3,798,178 A * | 3/1974 | Soderquist et al. | 502/174 |
| 3,905,917 A | 9/1975 | Nishino | |
| 4,065,406 A | 12/1977 | Nishino | |
| 4,149,996 A | 4/1979 | Manning | |
| 4,418,237 A | 11/1983 | Imai | |
| 4,435,607 A | 3/1984 | Imai | |
| 4,746,643 A | 5/1988 | Buonomo | |
| 4,788,371 A | 11/1988 | Imai | |
| 5,108,973 A | 4/1992 | Satek | |
| 5,510,557 A | 4/1996 | Gartside | |
| 5,545,787 A | 8/1996 | Cooper | |
| 5,827,496 A | 10/1998 | Lyon | |
| 6,326,523 B1 | 12/2001 | Stahl | |
| 6,891,138 B2 | 5/2005 | Dalton | |
| 7,067,455 B2 * | 6/2006 | Chen et al. | 502/325 |
| 7,074,977 B2 * | 7/2006 | Rapier et al. | 585/324 |
| 7,192,987 B2 | 3/2007 | Van Egmond | |
| 7,196,239 B2 | 3/2007 | Van Egmond | |
| 7,199,276 B2 | 4/2007 | Sher | |
| 2004/0092391 A1 | 5/2004 | Rokicki et al. | |
| 2007/0054801 A1 * | 3/2007 | Fridman et al. | 502/318 |

FOREIGN PATENT DOCUMENTS

| | | |
|---|---|---|
| JP | 1086944 A | 2/1986 |
| RU | 2157279 C1 | 10/2000 |
| RU | 2254162 C1 | 6/2005 |
| WO | 02068119 A1 | 9/2002 |
| WO | 0313715 A1 | 2/2003 |

* cited by examiner

*Primary Examiner*—Jerry Lorengo
*Assistant Examiner*—Jennifer A Smith

(57) ABSTRACT

An improved dehydrogenation catalyst bed system for olefin production utilizing classical processing techniques is disclosed. The catalyst bed system comprises a dehydrogenation catalyst comprising an active component selected from an oxide of a metal of Group 4 or Group 5 or Group 6 and combinations thereof and a support selected from aluminum oxide, aluminas, alumina monohydrate, alumina trihydrate, alumina-silica, transition aluminas, alpha-alumina, silica, silicate, aluminates, calcined hydrotalcites, zeolites and combinations thereof mixed with a first inert material selected from any material that is catalytically inactive when subjected to reaction conditions that can effect dehydrogenation of olefins and that has a high density and high heat capacity and that is not capable of producing heat during any stage of the dehydrogenation process, and the dehydrogenation catalyst plus the first inert material then being physically mixed with a secondary component comprising a heat-generating inert material and a carrier capable of supporting the heat-generating inert material, wherein the secondary component is catalytically inert with respect to dehydrogenation reactions or to cracking or to coking and generates heat after being exposed to reducing and/or to oxidizing reaction conditions.

19 Claims, No Drawings

CATALYTICALLY INACTIVE HEAT GENERATOR AND IMPROVED DEHYDROGENATION PROCESS

BACKGROUND

The present development relates to an improved dehydrogenation catalyst bed system for olefin production utilizing classical processing techniques. Specifically, the catalyst system comprises a chromia/alumina dehydrogenation catalyst that further includes physically mixing the catalyst with at least one other component that is catalytically inert with respect to dehydrogenation or side reactions such as cracking or coking but that generates heat after being exposed to reducing and/or to oxidizing reaction conditions.

Dehydrogenation of aliphatic hydrocarbons to produce their complementary olefins is a well-known process. In the typical Houdry CATOFIN® process, an aliphatic hydrocarbon, such as propane, is passed through a dehydrogenation catalyst bed where the hydrocarbon is dehydrogenated to its complementary olefin, such as propylene, the olefin is flushed from the bed, the catalyst is regenerated and reduced, and the cycle is repeated. (See, for example, U.S. Pat. No. 2,419,997 and incorporated herein by reference.)

The CATOFIN® dehydrogenation process is an adiabatic, cyclic process. Each cycle includes a catalyst reduction step, a dehydrogenation step, a step to purge the remaining hydrocarbon from the reactor, and finally a regeneration step with air. Following this, the cycle begins again with the reduction step.

The dehydrogenation reaction is highly endothermic. Therefore, during the dehydrogenation step the temperature at the top of the catalyst bed decreases by as much as 100° C. This decrease in temperature causes a decrease in paraffin conversion.

In order to reheat the catalyst bed and remove coke that has deposited on the catalyst during the dehydrogenation step, the reactor is purged of hydrocarbon and then undergoes a regeneration step with air heated to temperatures of up to 700° C. Heat is provided to the bed by the hot air that passes through the bed and also by the combustion of the coke deposits on the catalyst. Reduction of the catalyst, with a reducing gas such as hydrogen, prior to dehydrogenation step also provides some additional heat.

During regeneration, the hot air flows from the top of the catalyst bed to the bottom, and the regeneration cycle is relatively short, so there is a tendency for the top of the bed to be hotter than the bottom of the bed. The lower temperature in the bottom of the bed does not allow full utilization of the catalyst and thus the yield is lower that what would be otherwise expected. Also, the coke distribution in the catalyst bed, which is not easily controlled, affects the amount of heat added at each location and the resulting catalyst bed temperature profile. These factors make control of the temperature profile in the bed difficult.

In the conventional HOUDRY CATOFIN® process, the reactor contains a physical mixture of a chromia/alumina catalyst and an "inert". The volume ratio between the "inert" material and the catalyst depends on a number of factors including the type of hydrocarbon feed being used in the dehydrogenation process. For example, for a propane feed the "inert" material equal to about 50% of the total catalyst volume, whereas for an isobutane feed the volume of the "inert" can be as low as about 30% of the total catalyst bed volume.

The "inert" is typically a granular, alpha-alumina material of similar particle size to the catalyst that is catalytically inactive with respect to dehydrogenation or side reactions such as cracking or coking, but that has a high density and high heat capacity, so it can be used to store additional heat in the bed. The additional heat is then used during the dehydrogenation step. However, the "inert" is not capable of producing heat during any stage of the process.

Since dehydrogenation is a highly endothermic reaction, a constant challenge related to the Houdry process, and similar adiabatic non-oxidative dehydrogenation processes, has been to identify a commercially feasible means for improving the heat addition to the unit without using a catalytically active material that produces large quantities of unwanted side products. Thus, it would be advantageous to identify a catalyst additive that has a heat capacity and density comparable to the currently used alumina "inert", and that does not participate to any great extent in the dehydrogenation reaction or side reactions such as cracking or coking, and that can be physically mixed with the catalyst before loading, but that generates heat as needed during the operation.

SUMMARY OF THE INVENTION

The present development is a dehydrogenation catalyst bed system comprising a conventional chromia/alumina dehydrogenation catalyst that further includes at least one component that is catalytically inert with respect to dehydrogenation or side reactions such as cracking or coking but that generates heat after being exposed to reducing and/or to oxidizing reaction conditions. In an exemplary embodiment, the heat-generating inert component has a similar density and heat capacity to alpha-alumina. In a further exemplary embodiment, the catalyst system comprises a chromia/alumina catalyst physically mixed with a heat-generating inert component comprising copper oxide supported on alumina wherein the copper oxide comprises at least about 8 wt % of the heat-generating inert component.

DETAILED DESCRIPTION OF THE PREFERRED EMBODIMENT

The catalyst bed system of the present invention is intended for use in aliphatic hydrocarbon dehydrogenation reaction processes, and similar adiabatic non-oxidative dehydrogenation processes, specifically for the production of olefins. The catalyst bed system utilized in the process is a chromia/alumina dehydrogenation catalyst that further comprises a heat-generating component that is inert with respect to the dehydrogenation reaction or side reactions such as cracking or coking.

The equipment used for the dehydrogenation process includes a reactor bed wherein the bed defines a top section and a bottom section. In commercial practice, a catalyst is physically mixed with an inert, such as granular alpha-alumina, and the catalyst plus inert is then loaded into the reactor bed. An aliphatic hydrocarbon is fed into the catalyst bed as a gas feed at a preselected flow rate and such that the feed initially contacts the top section of the bed and exits after contact with the bottom section. For the purposes of example herein, the aliphatic hydrocarbon is propane and the target product is propylene.

For exemplary purposes only, the process generally follows the typical "Houdry" process as described in U.S. Pat. No. 2,419,997. The Houdry process includes a series of stages wherein the catalyst bed is evacuated, reduced with hydrogen and evacuated, then an aliphatic hydrocarbon is introduced and dehydrogenated, then the catalyst bed is steam purged and regenerated, and the cycle is repeated starting with the reduction stage.

As is known in the art, a catalyst generally has one or more active components dispersed on or compounded with a carrier or support. The support provides a means for increasing the surface area of the catalyst. Several compositions for dehydrogenation catalysts have been taught in the prior art, such as the catalyst taught in U.S. Pat. No. 3,488,402 (issued to Michaels et al., and incorporated herein by reference). The '402 catalyst comprises "alumina, magnesia, or a combination thereof, promoted with up to about 40% of an oxide of a metal" of Group 4, Group 5 or Group 6. (The terms "Group 4", "Group 5" and "Group 6" refer to the new IUPAC format numbers for the Periodic Table of the Elements. Alternative terminology, known in the art, includes the old IUPAC labels "Group IVA," "Group VA" and "Group VI-A", respectively, and the Chemical Abstract Services version of numbering as "Group IVB," "Group VB" and "Group VI-B", respectively.) Recommended carriers for dehydrogenation catalysts include aluminum oxide, aluminas, alumina monohydrate, alumina trihydrate, alumina-silica, transition aluminas, alpha-alumina, silica, silicate, aluminates, calcined hydrotalcites, zeolites and combinations thereof. For the present application, the catalyst may be prepared by any standard method known in the art, such as taught in U.S. Patent Application 20040092391, incorporated herein in its entirety by reference.

The active dehydrogenation catalyst is then physically mixed with a first inert material. This first inert material may be any material that is catalytically inactive with respect to dehydrogenation or side reactions, such as cracking or coking, and that has a high density and high heat capacity, but that is not capable of producing heat during any stage of the process. For the present application, an exemplary first inert material is a granular, alpha-alumina material of similar particle size to the catalyst. As is known in the art, the volume ratio between the first inert material and the catalyst depends on a number of factors including the type of hydrocarbon feed being used in the dehydrogenation process. In the present application, no particular volume ratio is prescribed, but rather the user may adjust the ratio as appropriate for the intended use.

In the present invention, the catalyst and the first inert material is then further physically combined with at least one secondary component. The secondary component must be catalytically inert with respect to dehydrogenation or side reactions such as cracking or coking but must generate heat after being exposed to reducing and/or to oxidizing reaction conditions.

More specifically, the secondary component comprises a heat-generating inert material and a carrier capable of supporting the heat-generating inert material. Exemplary carriers for the secondary component include, but are not limited to, aluminum oxide, aluminas, alumina monohydrate, boehmite, pseudo-boehmite, alumina trihydrate, gibbsite, bayerite, alumina-silica, transition aluminas, alpha-alumina, silica, silicate, aluminates, calcined hydrotalcites, zeolites, zinc oxide, chromium oxides, magnesium oxides and combinations thereof.

The heat-generating inert material may be selected from copper, chromium, molybdenum, vanadium, cerium, yttrium, scandium, tungsten, manganese, iron, cobalt, nickel, silver, bismuth and combinations thereof. The heat-generating inert material comprises from about 1 wt % to about 40 wt % of the total secondary component weight. In a more preferred embodiment, the heat-generating inert material comprises from about 4 wt % to about 20 wt % of the total secondary component weight; and in a most preferred embodiment, the amount of heat-generating inert material is from about 6 wt % to about 10 wt % of the total secondary component weight. Optionally, the secondary component may further comprise a promoter, such as an alkali, an alkaline earth metal, lithium, sodium, potassium, rubidium, cesium, beryllium, magnesium, calcium, strontium, barium and a combination thereof.

The secondary component is prepared by essentially the same methods known in the art for preparing a supported catalyst. For example, and without limitation, the secondary component may be prepared by precipitation of the secondary component carrier with the heat-generating inert material, or by impregnation of the secondary component carrier with the heat-generating inert material. Promoters may further be added with the heat-generating inert material, or may be otherwise added to the secondary component via methods known in the art for the addition of promoters. A representative preparation, without limitation, is alumina trihydrate (gibbsite) is pelletized as approximately 3/16" pellets, and then the gibbsite is calcined at about 550° C. for about 4 hours, and the calcined material is then impregnated with a saturated solution of copper nitrate, and the impregnated material is dried for about 4 hours at about 250° C. and is then calcined at from about 500° C. to 1400° C.

The catalyst bed system is then prepared by physically mixing or combining the catalyst, the first inert material and the secondary component. More specifically, the desired amount of catalyst is defined, and then is mixed with a predetermined amount of the first inert material and a predetermined amount of the secondary component. The amount of first inert material is essentially equal to the amount of inert material that would normally be combined with the catalyst less the amount of secondary component to be added. That is, the secondary component is added in such a manner as to be a complete or partial substitution for the first inert material. The secondary component does not affect the amount of catalyst added nor the relative ratio of catalyst to inert material in the resultant catalyst bed. In an exemplary embodiment, without limitation, the volume of catalyst used equals about 25% to about 75% of the volume of the first inert material plus secondary component or (vol. catalyst)/(vol. first inert material+vol. secondary component)=0.25 to 0.75.

The volume of the secondary component to be used should be equal to 20 to 100% of the volume of the first inert material plus secondary component or (vol. secondary component)/(vol. first inert material+ vol. secondary component)=0.20 to 1.0

The mixture is then loaded into the reactor in the same manner as traditional dehydrogenation catalysts are loaded.

In an improved Houdry process, the catalyst bed is evacuated and reduced with hydrogen. During this stage, the secondary component in the reactor bed generates additional heat that passes into the alumina-supported chromium oxide catalyst portion of the reactor bed. Then an aliphatic hydrocarbon is fed into the catalyst bed and is dehydrogenated upon contact with the alumina-supported chromium oxide catalyst portion of the reactor bed. Because the alumina-supported chromium oxide catalyst portion of the bed has been essentially pre-heated by the secondary component, the alumina-supported chromium oxide catalyst demonstrates improved conversion relative to a reactor bed that does not include the secondary component. The catalyst bed is steam purged and regenerated, and the cycle is repeated starting with the reduction stage. During the regeneration step, the secondary component may also generate additional heat. In a preferred embodiment, the secondary component is selected such that no significant negative effect on selectivity is observed.

The catalyst bed system of the present invention is intended for use in an adiabatic non-oxidative cyclic dehydrogenation process. The catalyst bed system differs from the catalyst bed systems of the prior art by requiring that the catalyst comprise a heat-generating component that is inert with respect to the dehydrogenation reaction or side reactions such as cracking or coking. It is understood that the composition of the catalyst and the specific processing conditions may be varied without exceeding the scope of this development.

What is claimed is:

1. A catalyst bed system for use in adiabatic, non-oxidative and cyclic dehydrogenation processes comprising:
   (a) a dehydrogenation catalyst comprising an active component and a support, wherein said active component is selected from an oxide of a metal of Group 4 or Group 5 or Group 6 and combinations thereof; and wherein said support is selected from aluminum oxide, aluminas, alumina monohydrate, alumina trihydrate, alumina-silica, transition aluminas, alpha-alumina, silica, silicate, aluminates, calcined hydrotalcites, zeolites and combinations thereof;
   (b) a first inert material selected from any material that is catalytically inactive when subjected to reaction conditions that can effect non-oxidative dehydrogenation for the production of olefins and that has a high density and high heat capacity and that is not capable of producing heat during any stage of the non-oxidative and cyclic dehydrogenation process; and
   (c) a secondary component comprising a heat-generating inert material and a carrier capable of supporting the heat-generating inert material, wherein said secondary component is catalytically inert in a first stage involving non-oxidative dehydrogenation, non-oxidative cracking or non-oxidative coking and generates heat after being exposed to reducing and/or to oxidizing reaction conditions in a second stage of the cyclic process; and
   said dehydrogenation catalyst, first inert material, and secondary component are separate, solid phase components that are physically mixed with each other to form the catalyst bed system and said catalyst bed system is subjected to a cyclic operation that comprises at least non-oxidative dehydrogenation in a first stage and reducing and/or oxidizing reaction conditions in a second stage.

2. The catalyst bed system of claim 1 wherein said heat-generating inert material is selected from copper, chromium, molybdenum, vanadium, cerium, yttrium, scandium, tungsten, manganese, iron, cobalt, nickel, silver, bismuth and combinations thereof, and wherein said heat-generating inert material comprises from about 1 wt % to about 40 wt % of the total secondary component weight.

3. The catalyst bed system of claim 1 wherein said secondary component carrier is selected from aluminum oxide, aluminas, alumina monohydrate, boehmite, pseudo-boehmite, alumina trihydrate, gibbsite, bayerite, alumina-silica, transition aluminas, alpha-alumina, silica, silicate, aluminates, calcined hydrotalcites, zeolites, zinc oxide, chromium oxides, magnesium oxides and combinations thereof.

4. The catalyst bed system of claim 1 wherein said secondary component further comprises a promoter selected from an alkali, an alkaline earth metal, lithium, sodium, potassium, rubidium, cesium, beryllium, magnesium, calcium, strontium, barium and a combination thereof.

5. The catalyst bed system of claim 1 wherein said dehydration catalyst, said first inert material, and said secondary component have a volume relationship defined by the equation:

$$\text{(vol. dehydration catalyst)/(vol. first inert material+ vol. secondary component)}=0.25 \text{ to } 0.75, \text{ and}$$

said first inert material and said secondary component have a volume relationship defined by the equation:

$$\text{(vol. secondary component)/(vol. first inert material+ vol. secondary component)}=0.20 \text{ to } 1.0.$$

6. A catalyst bed system for use in adiabatic, non-oxidative, and cyclic dehydrogenation processes comprising:
   an active catalyst component selected from an oxide of chromium on an alumina support;
   a granular, alpha-alumina first inert material having a similar particle size to said active catalyst component; and
   a secondary supported catalyst comprising a heat-generating inert material selected from the group consisting of copper, manganese and combinations thereof, and a carrier capable of supporting the heat-generating inert material, wherein said secondary supported catalyst is catalytically inert in a first stage involving non-oxidative dehydrogenation, non-oxidative cracking, or non-oxidative coking and generates heat after being exposed to reducing and/or to oxidizing reaction conditions in a second stage; and said dehydrogenation catalyst, first inert material, and secondary supported catalyst are separate solid phase components that are physically mixed with each other to form the catalyst bed system and said catalyst bed system is subjected to a cyclic operation that comprises at least non-oxidative dehydrogenation in a first stage and reducing and/or oxidizing reaction conditions in a second stage.

7. The catalyst bed system of claim 6 wherein said secondary component carrier is selected from aluminum oxide, aluminas, alumina monohydrate, boehmite, pseudo-boehmite, alumina trihydrate, gibbsite, bayerite, alumina-silica, transition aluminas, alpha-alumina, silica, silicate, aluminates, calcined hydrotalcites, zeolites, zinc oxide, chromium oxides, magnesium oxides and combinations thereof.

8. The catalyst bed system of claim 6 wherein said heat-generating inert material comprises from about 1 wt % to about 40 wt % of the total secondary component weight.

9. The catalyst bed system of claim 6 wherein said heat-generating inert material comprises from about 4 wt % to about 20 wt % of the total secondary component weight.

10. The catalyst bed system of claim 6 wherein said heat-generating inert material comprises from about 6 wt % to about 10 wt % of the total secondary component weight.

11. The catalyst bed system of claim 6 wherein said secondary component further comprises a promoter selected from an alkali, an alkaline earth metal, lithium, sodium, potassium, rubidium, cesium, beryllium, magnesium, calcium, strontium, barium and a combination thereof.

12. The catalyst bed system of claim 6 wherein said dehydration catalyst, said first inert material, and said secondary component have a volume relationship defined by the equation:

$$\text{(vol. dehydration catalyst)/(vol. first inert material+ vol. secondary component)}=0.25 \text{ to } 0.75, \text{ and}$$

said first inert material and said secondary component have a volume relationship defined by the equation:

$$\text{(vol. secondary component)/(vol. first inert material+ vol. secondary component)}=0.20 \text{ to } 1.0.$$

13. The catalyst bed system of claim 1 prepared by precipitating the secondary component carrier with the heat-generating inert material.

14. The catalyst bed system of claim 6 prepared by precipitating the secondary component carrier with the heat-generating inert material.

15. The catalyst bed system of claim 1 prepared by impregnating the secondary component carrier with the heat-generating inert material.

16. The catalyst bed system of claim 6 prepared by impregnating the secondary component carrier with the heat-generating inert material.

17. A process for the adiabatic, non-oxidative and cyclic dehydrogenation conversion of aliphatic hydrocarbons to olefins comprising:
   a) preparing a catalyst bed comprising as separate components physically combined with each other:
      i) a dehydrogenation catalyst comprising an active component and a support, wherein said active component is selected from an oxide of a metal of Group 4 or Group 5 or Group 6 and combinations thereof, and wherein said support is selected from aluminum oxide, aluminas, alumina monohydrate, alumina trihydrate, alumina-silica, transition aluminas, alpha-alumina, silica, silicate, aluminates, calcined hydrotalcites, zeolites and combinations thereof; and
      ii) a first inert material selected from any material that is catalytically inactive when subjected to reaction conditions that can effect non-oxidative dehydrogenation for the production of olefins and that has a high density and high heat capacity and that is not capable of producing heat during any stage of the non-oxidative and cyclic dehydrogenation process; and
      iii) a secondary component comprising a heat-generating inert material and a carrier capable of supporting the heat-generating inert material, wherein said secondary component is catalytically inert in a first stage involving non-oxidative dehydrogenation, non-oxidative cracking, or non-oxidative coking and generates heat after being exposed to reducing and/or to oxidizing reaction conditions in a second stage of the cyclic process, and wherein said dehydrogenation catalyst, first inert material and secondary component are separate, solid phase components that are physically mixed with each other to form the catalyst bed;
   b) reducing said catalyst bed wherein said secondary component generates heat that passes into said first inert material;
   c) passing an aliphatic hydrocarbon feed stream into said catalyst bed for dehydrogenation;
   d) dehydrogenating the aliphatic hydrocarbon feed stream, wherein the heat stored in the first inert material assists in the dehydrogenation;
   e) steam purging and regenerating said catalyst bed; and
   f) repeating step b) through step e) for multiple cycles in which aliphatic hydrocarbons are dehydrogenated to form olefins.

18. The dehydrogenation process of claim 17 wherein said reducing step b) includes passing hydrogen over the catalyst bed.

19. The dehydrogenation process of claim 17 wherein said regenerating step e) includes passing air heated to temperatures of up to 700° C. over the catalyst bed and wherein said secondary component generates additional heat that passes into said first inert material.

* * * * *

UNITED STATES PATENT AND TRADEMARK OFFICE
CERTIFICATE OF CORRECTION

PATENT NO. : 7,622,623 B2 Page 1 of 1
APPLICATION NO. : 11/218949
DATED : November 24, 2009
INVENTOR(S) : Fridman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1000 days.

Signed and Sealed this

Twenty-sixth Day of October, 2010

David J. Kappos
*Director of the United States Patent and Trademark Office*